(12) United States Patent
Taniyama et al.

(10) Patent No.: US 9,106,090 B2
(45) Date of Patent: Aug. 11, 2015

(54) METHOD FOR RECOVERING CAPACITY OF LITHIUM ION BATTERY (75) Inventors: Koichi Taniyama, Tokyo (JP); Kazunori Haraguchi, Tokyo (JP); Kyohei Shimoyama, Okazaki (JP)

(73) Assignees: MITSUBISHI JIDOSHA KOGYO KABUSHIKI KAISHA, Tokyo (JP); MITSUBISHI JIDOSHA ENGINEERING KABUSHIKI KAISHA, Okazaki-Shi (JP)

( * ) Notice: Subject to any disclaimer, the term of this patent is extended or adjusted under 35 U.S.C. 154(b) by 203 days.

(21) Appl. No.: 13/981,439

(22) PCT Filed: Nov. 25, 2011

(86) PCT No.: PCT/JP2011/077231
§ 371 (c)(1),
(2), (4) Date: Jul. 24, 2013

(87) PCT Pub. No.: WO2012/124211
PCT Pub. Date: Sep. 20, 2012

(65) Prior Publication Data
US 2014/0028264 A1     Jan. 30, 2014

(30) Foreign Application Priority Data
Mar. 14, 2011     (JP) ................. 2011-055867

(51) Int. Cl.
*H02J 7/00* (2006.01)
*H01M 10/42* (2006.01)
*H01M 2/18* (2006.01)
*G08B 21/08* (2006.01)
(Continued)

(52) U.S. Cl.
CPC ............ *H02J 7/0068* (2013.01); *H01M 4/364* (2013.01); *H01M 6/5005* (2013.01); *H01M 10/058* (2013.01); *H01M 10/0525* (2013.01); *H01M 10/425* (2013.01); *H01M 10/44* (2013.01); *H01M 10/48* (2013.01); *G01N 27/416* (2013.01); *G08B 21/08* (2013.01); *Y02E 60/122* (2013.01); *Y02T 10/7011* (2013.01)

(58) Field of Classification Search
CPC ........ H02J 7/00; H02J 7/0068; G01N 27/416; G08B 21/08; H01M 10/0525; H01M 10/42; H01M 10/44; H01M 10/058; H01M 10/48; H01M 10/425; H01M 4/364; H01M 6/5005; H01M 2/18; Y02T 10/7011; Y02E 60/122
USPC .............. 320/134, 136; 340/636.19; 324/432, 324/464
See application file for complete search history.

(56) References Cited

U.S. PATENT DOCUMENTS

| 6,503,663 | B1 * | 1/2003 | Song et al. | ..................... 429/331 |
| 2005/0069777 | A1 * | 3/2005 | Takami et al. | ................ 429/245 |

FOREIGN PATENT DOCUMENTS

| JP | 8-190934 A | 7/1996 |
| JP | 10-321827 A | 11/1998 |

(Continued)

*Primary Examiner* — Phallaka Kik
(74) *Attorney, Agent, or Firm* — Birch, Stewart, Kolasch & Birch, LLP (57) ABSTRACT

A method for recovering the capacity of a lithium ion battery determines whether or not the cause of degradation is a decrease in lithium ions; calculates the amount of the decrease in lithium ions; and connects a lithium ion replenishing electrode to a positive electrode or a negative electrode to release lithium ions corresponding to the amount of the decrease from the lithium ion replenishing electrode, thereby replenishing the lithium ion battery with lithium ions for recovery of the battery capacity.

4 Claims, 6 Drawing Sheets

(51) Int. Cl.
*G01N 27/416* (2006.01)
*H01M 10/0525* (2010.01)
*H01M 10/44* (2006.01)
*H01M 4/36* (2006.01)
*H01M 10/058* (2010.01)
*H01M 10/48* (2006.01)
*H01M 6/50* (2006.01)

(56) References Cited

FOREIGN PATENT DOCUMENTS

| JP | 2002-324585 A | 11/2002 |
| JP | 2009-543294 A | 12/2009 |
| WO | WO 2008/002626 A2 | 1/2008 |

* cited by examiner

METHOD FOR RECOVERING CAPACITY OF LITHIUM ION BATTERY

TECHNICAL FIELD

This invention relates to a method for recovering the capacity of a lithium ion battery.

BACKGROUND ART

A lithium ion battery is one of secondary batteries with nonaqueous electrolytes. With the lithium ion battery, a lithium metal oxide is used as an active material in a positive electrode, while a carbon material such as graphite is used as an active material in a negative electrode. During charging, lithium ions released from the active material of the positive electrode are absorbed to the active material of the negative electrode. During discharging, the lithium ions stored in the active material of the negative electrode are released and absorbed to the positive electrode. This movement of the lithium ions between the electrodes allows an electric current to flow between the electrodes. That is, with the lithium ion battery, the lithium ions moving between the electrodes are responsible for electric conduction. Since the lithium ion battery has a high energy density, this is used, for example, as a battery for an electric vehicle.

With such a lithium ion battery, lithium ions moving between the electrodes during use are precipitated(deposited) on the surface of the negative electrode to form a film, which is fixed there, with the result that lithium ions movable between the electrodes decrease. Consequently, the capacity of the battery may decline, that is, the battery may degrade.

As a solution to the degradation of the battery, a secondary battery with a nonaqueous electrolyte is known which has a third electrode provided with metallic lithium making no contact with an electrolytic solution (see, for example, Patent Document 1).

PRIOR ART DOCUMENTS

Patent Documents

Patent Document 1: JP-A-2002-324585

SUMMARY OF THE INVENTION

Problems to be Solved by the Invention

According to such a secondary battery with a nonaqueous electrolyte, lithium ions are supplied from the third electrode to make up for a capacity decrease, thereby recovering the capacity of the battery. When the discharge capacity has decreased to 48 Ah relative to the initial discharge capacity of 50 Ah, for example, the third electrode is energized to release lithium ions in an amount corresponding to the decrease of 2 Ah into the battery, whereby lithium ions moving between the electrodes are supplied to recover the discharge capacity.

In this case, however, the lithium ions may be replenished in so large an amount as to form lithium dendrites on the positive electrode, making recovery of the battery capacity impossible.

The present invention has been accomplished in an attempt to solve the problems of the conventional technology. It is an object of the present invention to provide a method for recovery of lithium ion battery capacity, which can recover the capacity of a lithium ion battery by supplying a suitable amount of lithium ions while suppressing the formation of lithium dendrites.

Means for Solving the Problems

The method for recovering the capacity of a lithium ion battery according to the present invention is a method for recovering capacity of a lithium ion battery including a positive electrode containing a first active material and a second active material which is base in terms of electrode potential as compared with the first active material, a negative electrode, an electrolytic solution, and a lithium ion replenishing electrode for releasing lithium ions, the method comprising: a determination step of comparing charge/discharge characteristics in an initial stage of the lithium ion battery with charge/discharge characteristics at a time of determination after a lapse of a predetermined period from the initial stage to determine a cause of degradation of the lithium ion battery, wherein if charge/discharge capacity in the initial stage and charge/discharge capacity at the time of determination, when electrode potential corresponding to the first active material is held as a potential difference between the positive electrode and the negative electrode during charging or discharging of the lithium ion battery, are equivalent to each other, and if the charge/discharge capacity, when electrode potential corresponding to the second active material is held as the potential difference, is lower at the time of determination than in the initial stage, it is determined that the cause of degradation is a decrease in lithium ions; a calculation step of calculating an amount of the decrease in lithium ions based on a difference between the charge/discharge capacity at the time of determination and the charge/discharge capacity in the initial stage when the electrode potential corresponding to the second active material is held as the potential difference; and a replenishment step of connecting the lithium ion replenishing electrode to the positive electrode or the negative electrode to release lithium ions corresponding to the amount of the decrease from the lithium ion replenishing electrode, thereby replenishing the lithium ion battery with lithium ions.

With the present invention, if it is determined that the cause of degradation is a decrease in lithium ions, the amount of the decrease in lithium ions is calculated based on the difference between charge/discharge capacity at the time of determination and charge/discharge capacity in the initial stage when the electrode potential corresponding to the second active material is held as the potential difference. By so doing, lithium ions in such a suitable amount as to suppress the formation of lithium dendrites can be replenished. Charge/discharge, charging/discharging, or a similar expression means at least one of charging and discharging. The term "in an (or the) initial stage" refers to a period of time, whether before use or after start of use, until the lithium ion battery begins to degrade.

It is preferred that if, in the determination step, the charge/discharge capacity, when electrode potential corresponding to the first active material is held as the potential difference, is found to be lower at the time of determination than in the initial stage, the amount of the decrease in lithium ions is not calculated in the calculation step, and the lithium ion replenishing electrode and the positive electrode or the negative electrode are not connected together in the replenishment step; or that if, in the determination step, the potential difference is found to be lower than the electrode potential corresponding to the second active material, the amount of the decrease in lithium ions is not calculated in the calculation step, and the lithium ion replenishing electrode and the positive electrode or the negative electrode are not connected together in the replenishment step. In such a case, the battery has degraded for a cause which is not a decrease in lithium ions because of precipitation of lithium ions. If lithium ions are replenished even in such a case, degradation of the battery is rather accelerated.

In a preferred embodiment of the present invention, the amount of electrons for releasing lithium ions corresponding to the amount of the decrease is calculated in the calculation step; a detection step of detecting whether or not a current corresponding to the amount of electrons has flowed from the positive electrode or the negative electrode into the lithium ion replenishing electrode is further provided; and when it is detected in the detection step that the current corresponding to the amount of electrons has flowed in, connection between the lithium ion replenishing electrode and the positive electrode or the negative electrode is released in the replenishment step.

Effects of the Invention

The method for recovering the capacity of a lithium ion battery according to the present invention can exhibit the excellent effect that the capacity of a lithium ion battery can be recovered by replenishing a suitable amount of lithium ions while suppressing the formation of lithium dendrites.

MODE FOR CARRYING OUT THE INVENTION

The lithium ion battery of the present invention will now be described using FIGS. 1(a), 1(b).

A lithium ion battery 1 has a battery case 2. The interior of the battery case 2 is filled with an electrolytic solution 3. A power generation element 4 is housed in the battery case 2. The power generation element 4 comprises a wound stack of a positive plate and a negative plate, with a separator interposed therebetween. In the present invention, the positive plate is called a positive electrode, and the negative plate is called a negative electrode. The positive electrode and the negative electrode are referred to collectively as the electrode(s).

With the power generation element 4, a positive electrode terminal 5 is connected to the positive plate of the power generation element 4, and a negative electrode terminal 6 is connected to the negative plate of the power generation element 4. These positive electrode and the negative electrode are held by a case cover 7, which is provided on top of the battery case 2, for example, in such a manner as to be sealed with a seal member.

The positive electrode and the negative electrode are each composed of a current collector comprising, for example, aluminum, and a positive electrode material or a negative electrode material coated on both surfaces of the current collector, the positive electrode material or the negative electrode material containing an active material, as will be described below.

The positive electrode, in the present embodiment, contains two or more active materials, and it suffices for the respective active materials to have electrode potentials, which differ from each other, relative to an electrolytic solution. Examples of the active material are metal oxides capable of absorbing and releasing lithium, such as metal oxides of a layered structure type, metal oxides and metallic compounds of a spinel type, and metal oxides of an oxidized acid salt type. As the layered structure type metal oxides, a lithium nickel composite oxide and a lithium cobalt composite oxide are named. The lithium nickel composite oxide includes not only an oxide containing lithium (Li) and nickel (Ni) as constituent metal elements, but also an oxide containing, in addition to lithium and nickel, at least one other metal element (i.e., a transition metal element or a typical metal element other than Li and Ni, or the transition metal element and the typical metal element), typically, in a proportion less than that of nickel (in terms of the atomic number; if two or more metal elements other than Li and Ni are contained, the proportion of their total amount is less than the proportion of Ni), as the constituent metal elements. The metal element other than Li and Ni is, for example, one or two or more metal elements selected from the group consisting of cobalt (Co), aluminum (Al), manganese (Mn), chromium (Cr), iron (Fe), vanadium (V), magnesium (Mg), titanium (Ti), zirconium (Zr), niobium (Nb), molybdenum (Mo), tungsten (W), copper (Cu), zinc (Zn), gallium (Ga), indium (In), tin (Sn), lanthanum (La), and cerium (Ce). The same can be said of the lithium cobalt composite oxide mentioned below and the lithium manganese composite oxide to be described later.

As the lithium nickel composite oxide, lithium nickelate is preferably named. Lithium cobaltate is preferably named as the lithium cobalt composite oxide.

An example of the spinel type metal oxide is a lithium manganese composite oxide such as lithium manganate. Examples of the oxidized acid salt type metal oxides are lithium iron phosphate, lithium manganese phosphate, and lithium silicon phosphate.

In the present embodiment, lithium cobaltate (second active material) and lithium manganate (first active material) are used as the active materials for the positive electrode.

Examples of the active material for the negative electrode are metallic lithium, lithium alloys, metal oxides, metal sulfides, metal nitrides, and carbon materials such as graphite. Examples of the metal oxides are those having irreversible capacity, such as tin oxides and silicon oxides. Graphite as the carbon material may be artificial graphite or natural graphite. In the present embodiment, graphite is used as the active material for the negative electrode.

The positive electrode material and the negative electrode material may contain other substances. For example, they may contain binders such as polyvinylidene fluoride, conductivity improvers such as acetylene black, and electrolytes (for example, lithium salts (supporting electrolytes) and ion conductive polymers). When the ion conductive polymer is contained, a polymerization initiator for polymerizing the above-mentioned polymer may be contained.

As the electrolytic solution 3, a polar solvent is named. Examples of such a polar solvent are ethylene carbonate (EC), propylene carbonate (PC), dimethyl carbonate (DMC), diethyl carbonate (DEC), γ-butyrolactone, sulfolane, dimethyl sulfoxide, acetonitrile, dimethylformamide, dimethylacetamide, 1,2-dimethoxyethane, 1,2-diethoxyethane, tetrahydrofuran, 2-methyltetrahydrofuran, dioxolane, and methyl acetate. Alternatively, a mixture of them may be used.

The polar solvent may contain a metal salt. Examples of the metal salt are lithium salts, such as $LiPF_6$, $LiPF_3(C_2F_5)_3$, $LiBF_4$, $LiAsF_6$, $LiClO_4$, $LiSCN$, $LiI$, $LiCF_3SO_3$, $LiCl$, $LiBr$, and $LiCF_3CO_2$, or mixtures of them.

In the present embodiment, ethylene carbonate (EC), dimethyl carbonate (DMC) or diethyl carbonate (DEC) is used as the electrolytic solution 3, and $LiPF_6$ is contained as the metal salt.

A third electrode 11 is held by the case cover 7 for the battery case 2. The third electrode 11 is in contact with the electrolytic solution 3. As the active material for the third electrode 11, one which can release lithium ions is named, such as metallic lithium, lithium titanate, or lithium silicide. In the present embodiment, metallic lithium is used as the active material for the third electrode 11. The third electrode 11 may also contain the aforementioned binder. The preferred content of the binder, if contained, is 5% or less, preferably 1% or less, based on the weight of the entire third electrode 11, because the content may be such that if the battery degrades, the third electrode 11 can release lithium ions. Since it suffices that the third electrode 11 can release lithium ions upon degradation of the battery, moreover, the content is preferably 5% or less, based on the weight of the entire third electrode 11, of the conductive materials contained in the third electrode 11 (i.e., the conductive materials contained in the current collector and the active material and, if the conductivity improver is contained, the conductivity improver is also included).

The third electrode 11 and the positive electrode, namely, the positive electrode terminal 5, are connected via a switching element 12 installed outside the battery case 2. A control unit 13 controls the opening and closing actions of the switching element 12 based on the discharge curve (to be described in detail later) of the lithium ion battery 1, as will be explained below.

The control unit 13 determines the cause of degradation of the lithium ion battery 1 based on the discharge curve of the lithium ion battery 1. If the control unit 13 determines that the cause of degradation is a deficiency of lithium ions within the battery upon precipitation of lithium ions, as will be described in detail below, the control unit 13 finds the amount of lithium ions lost to the lithium ion battery 1 as a result of precipitation. Then, the control unit 13 controls the switching element 12 so as to be closed, for the purpose of replenishing lithium ions. Thus, the positive electrode and the third electrode 11 are connected together and, because of the electrode potential difference between the positive electrode and the third electrode 11, lithium ions are supplied from the third electrode 11 to the positive electrode and absorbed to the positive electrode. As a result, lithium ions which the lithium ion battery 1 has lacked can be replenished, and the capacity of the lithium ion battery can be recovered.

A concrete explanation will be offered. Initially, the control unit 13 starts control upon entry of a signal showing the start of control from a battery control unit or the like (not shown) which exercises the integrated control of the lithium ion battery. The signal showing the start of control is entered from the battery control unit, for example, when the total operating time of the lithium ion battery exceeds a threshold value, or when the capacity of the lithium ion battery exceeds a threshold value.

When starting control, the control unit 13 initially determines the cause of degradation from a curve showing the voltage relative to the discharge capacity during discharging of the lithium ion battery 1 (the curve is designated as the discharge curve). The discharge curve of the lithium ion battery 1 is entered into the control unit 13, together with the signal showing the start of control, from the battery control unit or the like (not shown) which exercises control over the lithium ion battery 1.

Figure 2:
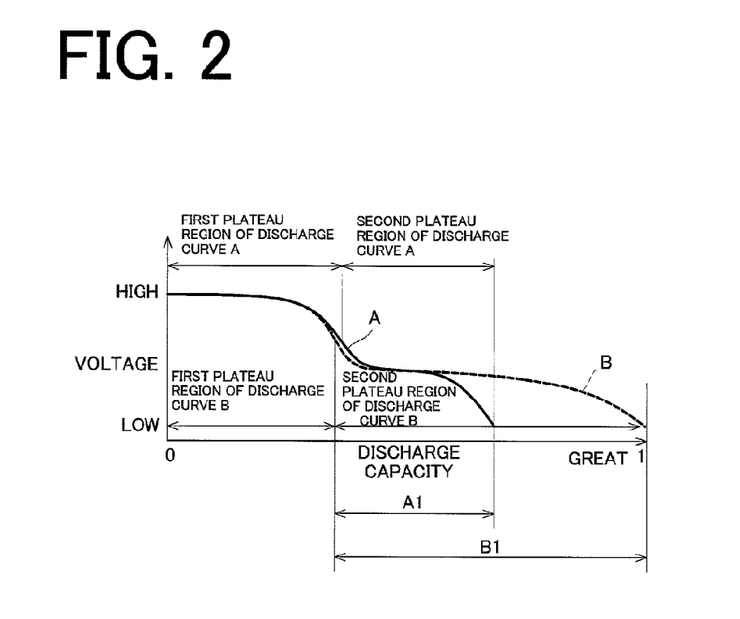
FIG. 2 is a graph showing the relationship between the discharge capacity and the voltage during discharging of the lithium ion battery according to the present embodiment.

In the present embodiment, the discharge curve is as shown in FIG. 2. In FIG. 2, the discharge capacity of 0 means a substantially completely charged state. FIG. 2 shows together the discharge curve A of the lithium ion battery 1 after degradation (i.e., the discharge curve inputted to the control unit 13, along with the signal showing the start of control over the battery, from the battery control unit), and the discharge curve B of the lithium ion battery 1 in the initial stage. The discharge curve A and the discharge curve B in the initial stage each initially show a nearly constant voltage with respect to the discharge capacity, but then as the discharge capacity increases, the voltage suddenly drops in the meantime. Thereafter, the voltage takes a nearly constant value again, whereafter the capacity is exhausted, and the voltage drops suddenly.

Figure 3:
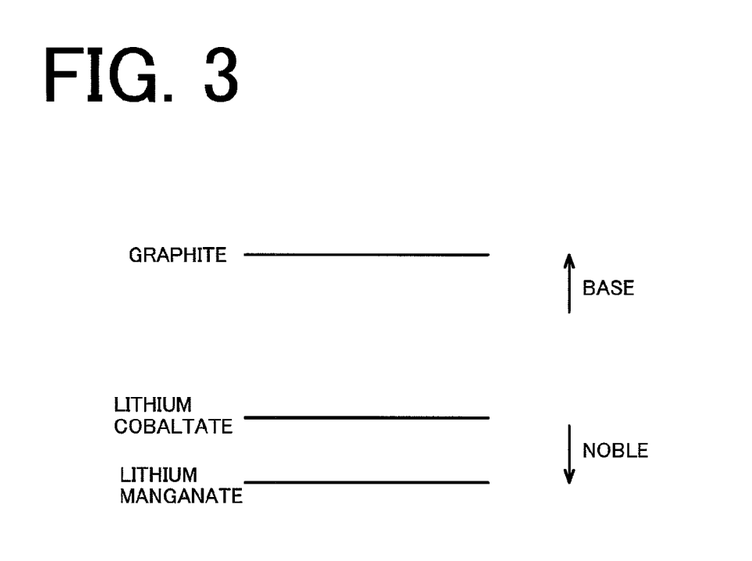
FIG. 3 is a view showing the electrode potential of a material for a positive electrode relative to a material for a negative electrode in the lithium ion battery according to the present embodiment.

Such discharge curves will be explained using FIG. 3. FIG. 3 shows the states of the electrode potentials of the respective electrode materials in the present embodiment.

As shown in FIG. 3, graphite used as the active material of the negative electrode is base compared with lithium cobaltate and lithium manganate used as the active materials of the positive electrode. Thus, lithium ions tend to be released from graphite. The released lithium ions are initially absorbed to lithium manganate which is noble compared with lithium cobaltate. Then, the lithium ions are absorbed to the total capacity content of lithium manganate and, when lithium ions are not absorbed to lithium manganate any more, they are then absorbed to lithium cobaltate. In the present embodiment, as described above, the two types of active materials are contained in the positive electrode. Thus, the discharge curve changes in potential stepwise with the discharge capacity in accordance with the respective active materials.

That is, with the discharge curves A, B, when discharging begins, lithium ions are absorbed to lithium manganate, so that the voltage of the discharge curve (potential difference between the positive electrode and the negative electrode) is held at the electrode potential of lithium manganate. A region of the discharge curve held at the electrode potential of lithium manganate is designated as a first plateau region (a region where the voltage during charging or discharging is held at the electrode potential corresponding to the first active material). Then, lithium ions are absorbed to all the lithium manganate of the positive electrode, whereupon lithium ions are absorbed to lithium cobaltate. As a result, the voltage of the discharge curve suddenly drops from the electrode potential of lithium manganate, and is held at the electrode potential of lithium cobaltate which is lower than the electrode potential of lithium manganate. A region of the discharge curve held at the electrode potential of lithium cobaltate is designated as a second plateau region (a region where the voltage during charging or discharging is held at the electrode potential corresponding to the second active material). When all lithium ions are absorbed to lithium cobaltate, the voltage becomes zero. In the present embodiment, two or more active materials are contained in the positive electrode, as mentioned above. Consequently, such a first plateau region and such a second plateau region can be formed in the discharge curve.

In this case, as shown in FIG. 2, the discharge curve A representing the post-degradation status has a shorter second plateau region than does the discharge curve B representing the initial-stage status. That is, the post-degradation discharge curve A shows a less discharge capacity in the lithium cobaltate on the low-voltage side than the initial-stage discharge curve B. This is because lithium ions are precipitated owing to the use of the lithium ion battery, and lithium ions movable between the electrodes decrease, so that even if lithium cobaltate is still able to absorb lithium ions, discharging ends.

As note above, the difference between the discharge curve B in the initial stage and the discharge curve A after use in FIG. 2 reflects a deficiency of lithium ions due to precipitation of lithium ions.

Figure 4:
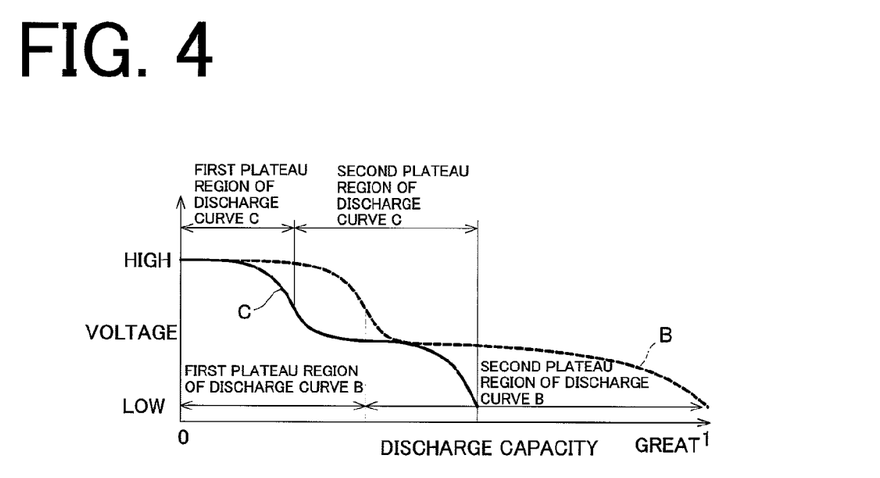
FIG. 4 is a graph showing the relationship between the discharge capacity and the voltage during discharging of the lithium ion battery when partial peeling of the electrode occurred.
Figure 5:
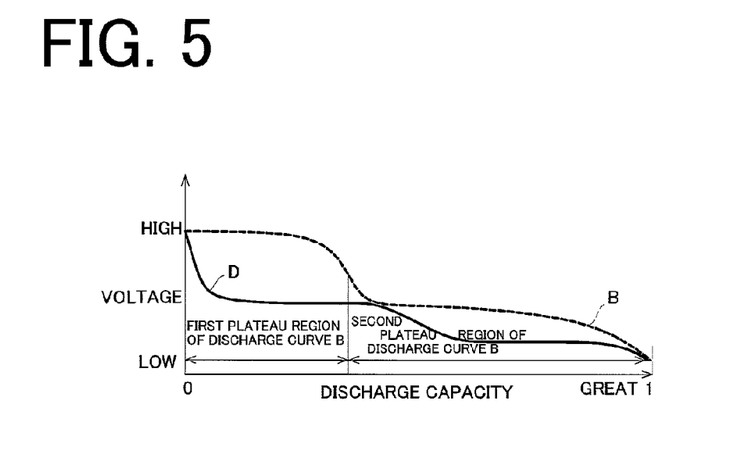
FIG. 5 is a graph showing the relationship between the discharge capacity and the voltage during discharging of the lithium ion battery when separation of an electrolytic solution occurred.

Other causes of degradation of the lithium ion battery are considered to include partial peeling due to chipping of the electrode, separation of the electrolyte, etc. If such partial peeling due to chipping of the electrode occurs, both of lithium manganate and lithium cobaltate simultaneously chip off, leading to a decrease in the amount of the positive electrode itself. In this case, therefore, both a first plateau region and a second plateau region shorten as compared with the discharge curve B in the initial stage, as in a discharge curve C shown in FIG. 4. If separation of the electrolyte occurs, on the other hand, the voltage sharply decreases immediately after start of discharging, as in a discharge curve D shown in FIG. 5, because the internal resistance of the lithium ion battery rises because of the separation of the electrolyte.

As seen above, the discharge curve of the lithium ion battery differs according to each cause of degradation.

Figure 1:
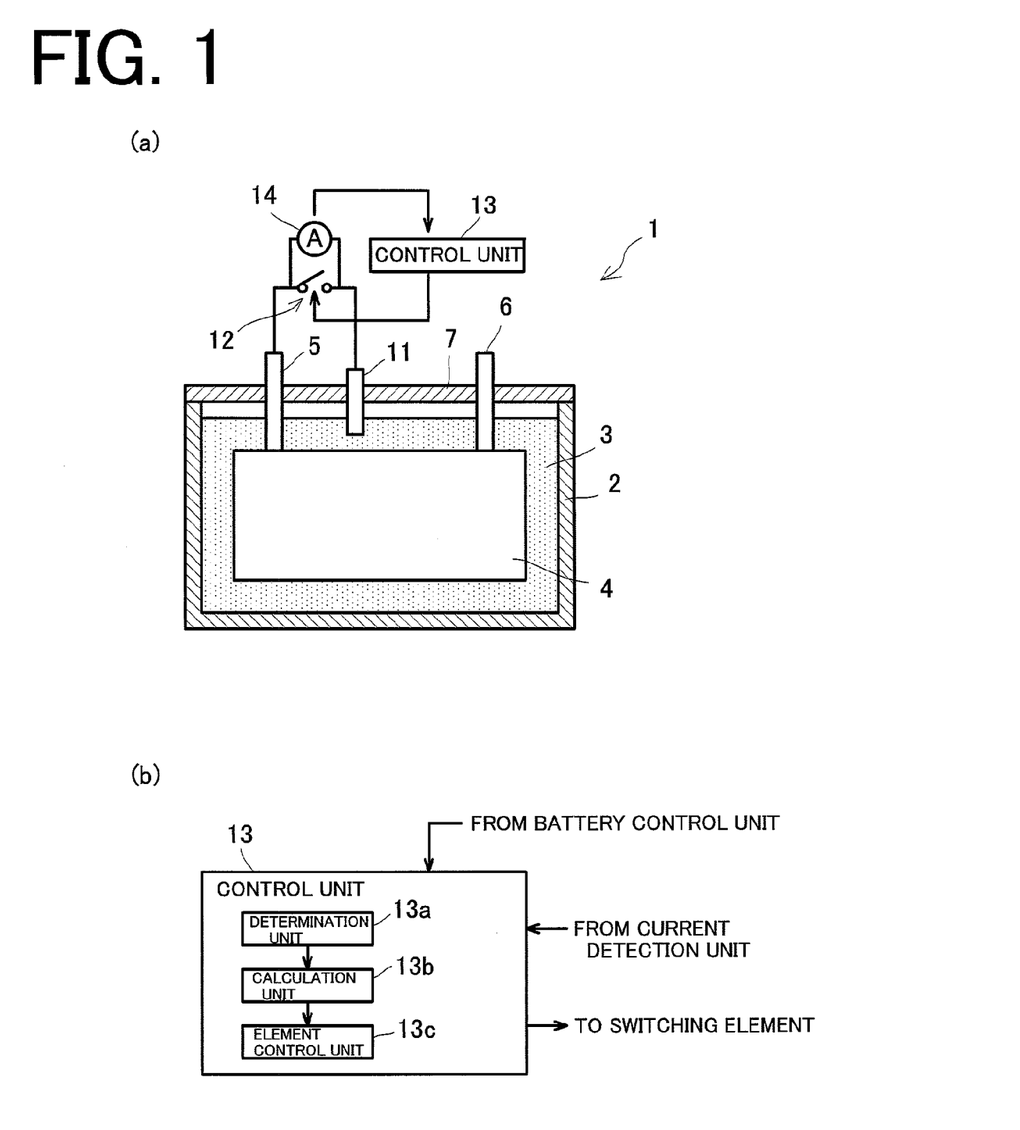
FIGS. 1(a), 1(b) are schematic views showing the structure of a lithium ion battery according to the present embodiment.

Based on the difference in the discharge curve due to the cause of degradation, a determination unit 13a of the control unit 13 shown in FIG. 1(b) determines the cause of degradation (determination step). That is, the determination unit 13a compares the charge/discharge characteristics in the initial stage of the lithium ion battery with the charge/discharge characteristics at the time of determination after a lapse of a predetermined period from the initial stage to determine the cause of degradation of the lithium ion battery. The determination unit 13a prestores the initial-stage discharge curve B in a recording unit or the like. The determination unit 13a acquires the discharge curve B from the recording unit, and compares it with the discharge curve A inputted from the battery control unit. If the discharge curve A reveals an abrupt voltage drop immediately after start of discharging, namely, if the voltage during charging or discharging of the lithium ion battery is lower than the electrode potential corresponding to the second active material, the determination unit 13a determines that the separation of the electrolyte has occurred.

If the comparison by the determination unit 13a between the discharge curve B and the discharge curve A shows the length of the first plateau region of the discharge curve A to be shorter than the length of the first plateau region of the discharge curve B in the initial stage, the determination unit 13a determines that degradation is attributed to a factor other than a decrease in lithium ions due to precipitation of lithium ions, such as peeling of the electrode. That is, if the charge/discharge capacity when the electrode potential corresponding to the first active material is held as the potential difference is found to be less at the time of the determination than in the initial stage, it is determined that degradation is attributed to a factor other than a decrease due to the precipitation of lithium ions. Concretely, the control unit 13 acquires the discharge capacity during the period from the start of discharging until attainment of an intermediate potential, which is intermediate between the electrode potential of lithium manganate and the electrode potential of lithium cobaltate, as the discharge capacity of the first plateau region (i.e., discharge capacity corresponding to the difference between the first plateau regions). The same is true for the length of the first plateau region to be described below. If the first plateau region of the discharge curve A is less than 90% of the first plateau region of the discharge curve B in the initial stage, a determination is made that degradation is ascribed to a factor other than a decrease in lithium ions due to their precipitation, such as peeling of the electrode.

If the comparison by the determination unit 13a between the discharge curve A and the discharge curve B in the initial stage shows that the length of the first plateau region of the discharge curve A is nearly the same as (equivalent to) the length of the first plateau region of the discharge curve B in the initial stage, and that the second plateau region of the discharge curve A is shorter than the second plateau region of the discharge curve B in the initial stage, the determination unit 13a determines that a decrease in lithium ions due to their precipitation has occurred. That is, if the charge/discharge capacity in the initial stage and that at the time of determination, when the electrode potential corresponding to the first active material is held, are equivalent to each other, and if the charge/discharge capacity when the electrode potential corresponding to the second active material is held is lower at the time of determination than in the initial stage, the determination unit 13a determines that the cause of degradation is a decrease in lithium ions. Concretely, when the length of the first plateau region of the discharge curve A is 90% to 100% of the first plateau region of the discharge curve B in the initial stage, and when the second plateau region of the discharge curve A is 0% to 80% of the second plateau region of the discharge curve B in the initial stage, the control unit 13 determines that a decrease in lithium ions due to their precipitation has occurred. As for the length of the second plateau region, discharge capacity for the range from the intermediate potential, which is intermediate between the electrode potential of lithium manganate and the electrode potential of lithium cobaltate, until the final potential as a half of the electrode potential of lithium cobaltate is acquired as the discharge capacity of the second plateau region (i.e., discharge capacity corresponding to the difference between the second plateau regions).

When the determination unit 13a determines that a decrease in lithium ions due to their precipitation has occurred, a determination signal is inputted to a calculation unit 13b of the control unit 13. The calculation unit 13b calculates the difference between discharge capacities corresponding to the second plateau regions of the discharge curve A and the discharge curve B (calculation step). That is, the calculation unit calculates the amount of the decrease in lithium ions based on the difference between the charge/discharge capacity at the time of determination and that in the initial stage when the electrode potential corresponding to the second active material is held. Concretely, the calculation unit 13b subtracts the discharge capacity (A1) corresponding to the second plateau region of the discharge curve A during use from the discharge capacity (B1) corresponding to the second plateau region of the discharge curve B in the initial stage. From the obtained difference in discharge capacity, the calculation unit 13b calculates the amount of lithium ions which has become deficient because of precipitation. Since the discharge capacity is expressed in Ah, the calculation unit 13b can find the amount of electrons corresponding to the deficiency in the amount of lithium ions based on this discharge capacity.

When the calculation unit 13b calculates the amount of electrons corresponding to the deficient lithium ion amount in the above-mentioned manner, an element control unit 13c of the control unit 13 inputs a signal for holding the switching element 12 in a closed state to the switching element 12 to bring the switching element 12 into the closed state, thereby establishing an electrical connection between the positive electrode terminal 5 and the third electrode (replenishment step). By so doing, lithium ions are released from the third electrode to supply lithium ions to the lithium ion battery 1.

The element control unit 13c thus electrically connects the positive electrode terminal 5 and the third electrode 11, and a current flowing between the positive electrode terminal 5 and the third electrode 11 is detected by a current detection unit 14 (in the present embodiment, ammeter) (detection step). The element control unit 13c determines, from the detected amount of current, whether or not a desired amount of electrons has flowed. When the desired amount of electrons has flowed as a current, the element control unit 13c controls the switching element 12 to be opened, thereby stopping the supply of lithium ions to the lithium ion battery 1.

When the determination unit 13a has determined that the cause of degradation is the separation of the electrolyte or the peeling of the electrode, the element control unit 13c holds the switching element 12 in the open state.

In the present embodiment, as described above, the first active material and the second active material are contained in the positive electrode, and the second plateau of the second active material is detected, whereby the insufficient amount of lithium ions can be detected accurately. Thus, lithium ions are not supplied in so large an amount as to form dendrites within the battery. Moreover, lithium is supplied in such a suitable amount that the lithium ion battery can be recovered from degradation.

In the present embodiment, moreover, so long as the lithium ion battery degrades for lack of lithium ions, the control unit 13 can supply lithium ions in a suitable amount. Hence, lithium ions are not supplied in so large an amount as to form dendrites within the battery. Moreover, lithium is supplied in such a suitable amount that the lithium ion battery can be recovered from degradation.

In the present embodiment, the first active material (lithium manganate, in the present embodiment) and the second active material (lithium cobaltate, in the present embodiment), which is base in terms of electrode potential as compared with the first active material, are mixed in predetermined amounts to form the positive electrode, so that the cause of degradation can be identified as described above. That is, if the positive electrode is produced without mixing the first active material and the second active material, unlike the present embodiment, no plateau is formed in the discharge curve, so that the cause of degradation cannot be identified. Thus, even if peeling of the electrode has occurred, for example, replenishment of lithium ions may take place. This is not preferred, because the formation of dendrites is caused, and degradation of the battery is accelerated.

When the electrode is to be formed only from lithium manganate, moreover, the desired battery potential may fail to be obtained. In the present embodiment, on the other hand, lithium cobaltate with a higher standard electrode potential than that of lithium manganate is mixed, whereby the desired battery potential can be obtained.

To obtain the above-mentioned effect, the mixing ratio between the first active material and the second active material is preferably such that the second active material is contained in a proportion of 10 to 40% based on the weight of the positive electrode. This range makes it easy to identify the cause of degradation and makes it possible to obtain the desired battery potential. The second active material content of less than 10% based on the weight of the positive electrode poses difficulty in developing a second plateau, makes it difficult to identify the cause of degradation, and may make it impossible to calculate the necessary amount of lithium ions. If the second active material is contained at a ratio of more than 40% based on the weight of the positive electrode, on the other hand, the desired battery potential cannot be obtained.

If the electrode is formed only from lithium cobaltate, the cost will be high. However, the mixing of lithium manganate, particularly as in the present embodiment, can cut down the manufacturing cost of the electrode.

With the present embodiment, as mentioned above, in releasing lithium ions from the third electrode 11, it suffices simply to connect the third electrode 11 and the positive electrode terminal 5. By this means, lithium ions can be replenished without the need for power, and the amount lost by degradation can be recovered.

According to the present embodiment, the positive electrode terminal 5 and the third electrode 11 are connected together, but this is not limitative. The negative electrode terminal 6 and the third electrode 11 may be connected together, if lithium ions can be released from the third electrode 11. However, the connection between the positive electrode terminal 5 and the third electrode 11 facilitates the release of lithium ions.

According to the present embodiment, the cause of degradation and the amount of decrease in lithium ions are determined from the voltage curves showing the relationship between the discharge capacity and the voltage during discharging, but this is not limitative. The cause of degradation and the amount of decrease in lithium ions may be determined from voltage curves showing the relationship between the charged capacity and the voltage during charging.

For example, the negative electrode, rather than the positive electrode, may be configured to contain the first active material and the second active material which is noble in terms of electrode potential as compared with the first active material. In this case, the amount of decrease in lithium ions may be calculated by subtracting the length, which corresponds to the electrode potential of the first active material with respect to the positive electrode, in the voltage curve relative to the amount of charge during charging of the lithium ion battery from the length, which corresponds to the electrode potential of the first active material with respect to the positive electrode, in the voltage curve in the initial stage during charging of the lithium ion battery.

In the present embodiment, the two active materials are contained in the positive electrode, but this is not limitative. For example, three or more active materials may be contained. Moreover, lithium cobaltate is contained as the second active material, but this is not limitative. For example, a so-called ternary electrode material comprising cobalt, manganese and nickel at an element ratio of 1:1:1 may be used. That is, two or more active materials with different electrode potentials may be contained.

Figure 6:
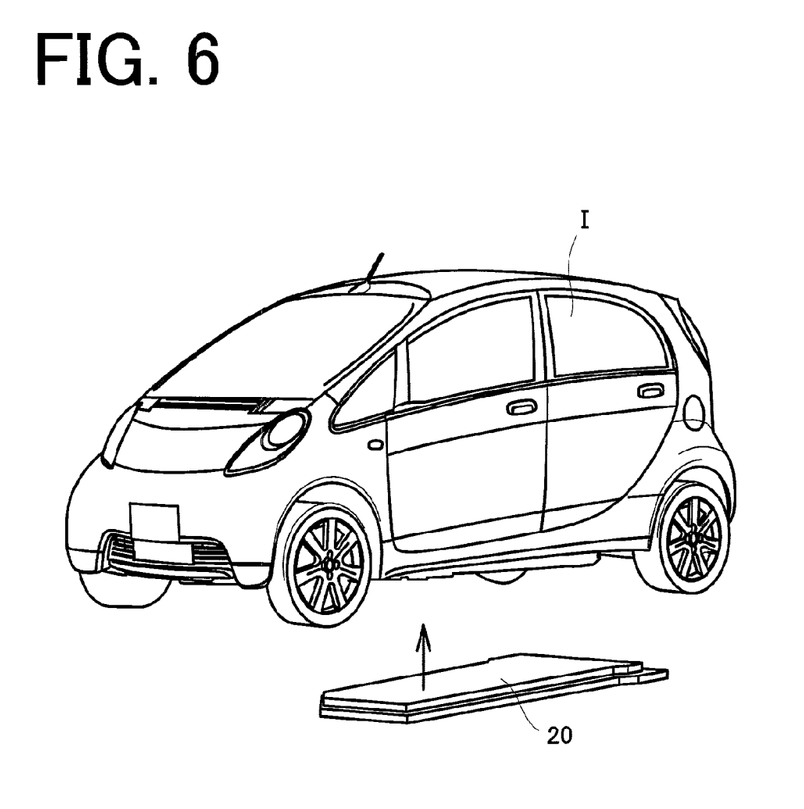
FIG. 6 is a schematic view of a vehicle loaded with the lithium ion battery of the present invention.

Such a lithium ion battery can be installed on a vehicle I, in a configuration in which a plurality of the lithium ion batteries are integrated into a battery pack and mounted within a battery case 20, for example, as shown in FIG. 6.

EXPLANATIONS OF LETTERS OR NUMERALS

1 Lithium ion battery
2 Battery case

3 Electrolytic solution
4 Power generation element
5 Positive electrode terminal
6 Negative electrode terminal
7 Case cover
11 Third electrode
12 Switching element
13 Control unit

The invention claimed is:

1. A method for recovering capacity of a lithium ion battery including
a positive electrode containing a first active material and a second active material which is base in terms of electrode potential as compared with the first active material,
a negative electrode,
an electrolytic solution, and
a lithium ion replenishing electrode for releasing lithium ions, the method comprising:
a determination step of comparing charge/discharge characteristics in an initial stage of the lithium ion battery with charge/discharge characteristics at a time of determination after a lapse of a predetermined period from the initial stage to determine a cause of degradation of the lithium ion battery,
wherein if charge/discharge capacity in the initial stage and charge/discharge capacity at the time of determination, when electrode potential corresponding to the first active material is held as a potential difference between the positive electrode and the negative electrode during charging or discharging of the lithium ion battery, are equivalent to each other, and if the charge/discharge capacity, when electrode potential corresponding to the second active material is held as the potential difference, is lower at the time of determination than in the initial stage, it is determined that the cause of degradation is a decrease in lithium ions;
a calculation step of calculating an amount of the decrease in lithium ions based on a difference between the charge/discharge capacity at the time of determination and the charge/discharge capacity in the initial stage when the electrode potential corresponding to the second active material is held as the potential difference; and
a replenishment step of connecting the lithium ion replenishing electrode to the positive electrode or the negative electrode to release lithium ions corresponding to the amount of the decrease from the lithium ion replenishing electrode, thereby replenishing the lithium ion battery with lithium ions.

2. The method for recovering capacity of a lithium ion battery according to claim 1, wherein
if, in the determination step, the charge/discharge capacity, when electrode potential corresponding to the first active material is held as the potential difference, is found to be lower at the time of determination than in the initial stage,
the amount of the decrease in lithium ions is not calculated in the calculation step, and the lithium ion replenishing electrode and the positive electrode or the negative electrode are not connected together in the replenishment step.

3. The method for recovering capacity of a lithium ion battery according to claim 1, wherein
if, in the determination step, the potential difference is found to be lower than the electrode potential corresponding to the second active material,
the amount of the decrease in lithium ions is not calculated in the calculation step, and the lithium ion replenishing electrode and the positive electrode or the negative electrode are not connected together in the replenishment step.

4. The method for recovering capacity of a lithium ion battery according to claim 1, wherein
an amount of electrons for releasing lithium ions corresponding to the amount of the decrease is calculated in the calculation step,
a detection step of detecting whether or not a current corresponding to the amount of electrons has flowed from the positive electrode or the negative electrode into the lithium ion replenishing electrode is further provided, and
when it is detected in the detection step that the current corresponding to the amount of electrons has flowed in, connection between the lithium ion replenishing electrode and the positive electrode or the negative electrode is released in the replenishment step.

* * * * *